(12) United States Patent
Muraoka et al.

(10) Patent No.: US 10,492,098 B2
(45) Date of Patent: Nov. 26, 2019

(54) TERMINAL, BASE STATION, AND METHOD FOR THE SAME

(71) Applicant: NEC Corporation, Tokyo (JP)

(72) Inventors: Kazushi Muraoka, Tokyo (JP); Hiroto Sugahara, Tokyo (JP)

(73) Assignee: NEC CORPORATION, Minato-ku, Tokyo (JP)

( * ) Notice: Subject to any disclaimer, the term of this patent is extended or adjusted under 35 U.S.C. 154(b) by 0 days.

(21) Appl. No.: 15/743,156

(22) PCT Filed: May 16, 2016

(86) PCT No.: PCT/JP2016/002376
§ 371 (c)(1),
(2) Date: Jan. 9, 2018

(87) PCT Pub. No.: WO2017/010030
PCT Pub. Date: Jan. 19, 2017

(65) Prior Publication Data
US 2018/0213438 A1    Jul. 26, 2018

(30) Foreign Application Priority Data

Jul. 15, 2015 (JP) ................................ 2015-141124

(51) Int. Cl.
*H04W 28/06* (2009.01)
*H04W 72/04* (2009.01)
(Continued)

(52) U.S. Cl.
CPC .......... *H04W 28/06* (2013.01); *H04W 8/005* (2013.01); *H04W 72/04* (2013.01);
(Continued)

(58) Field of Classification Search
None
See application file for complete search history.

(56) References Cited

U.S. PATENT DOCUMENTS

2016/0066305 A1*  3/2016  Chae ................... H04J 1/02
                                              370/330
2016/0338095 A1*  11/2016 Faurie ............... H04W 28/0278
(Continued)

FOREIGN PATENT DOCUMENTS

JP    2015-012405 A    1/2015
WO    2016/076301 A1   5/2016

OTHER PUBLICATIONS

"Discussion on UE-to-NW Relay Concurrent Processes", Intel Corporation, 3GPP TSG RAN WG1 Meeting #81, R1-152628, May 25-29, 2015, 6 pages, Fukuoka, Japan.
(Continued)

*Primary Examiner* — Candal Elpenord
(74) *Attorney, Agent, or Firm* — Sughrue Mion, PLLC

(57) ABSTRACT

A transmitting terminal (1A) transmits first D2D control information (522, 523) in one or more subframes within a first subframe pool (511) within a first D2D control period (501) and performs data transmission (531-534) in accordance with the first D2D control information (522, 523) in one or more subframes within a second subframe pool (512) within the first D2D control period (501). The first D2D control information (522, 523) contains a second information element indicating whether the first D2D control information (522, 523) is valid in at least one D2D control period (502, 503) occurring after the first D2D control period (501). This makes it possible to contribute, for example, to reducing failure in reception of scheduling assignment information that is transmitted in a radio resource region for control in a periodic D2D control period and that specifies D2D transmission resources.

17 Claims, 14 Drawing Sheets

(51) Int. Cl.
H04W 92/18 (2009.01)
H04W 76/14 (2018.01)
H04W 8/00 (2009.01)
H04W 88/06 (2009.01)

(52) U.S. Cl.
CPC ..... H04W 72/0406 (2013.01); H04W 72/048 (2013.01); H04W 72/0446 (2013.01); H04W 76/14 (2018.02); H04W 92/18 (2013.01); H04W 88/06 (2013.01)

(56) References Cited

U.S. PATENT DOCUMENTS

2017/0195995 A1\* 7/2017 Zhu .................. H04W 72/04
2017/0223711 A1\* 8/2017 Wang ................ H04W 72/02
2017/0257876 A1\* 9/2017 Loehr ................ H04L 5/0044

OTHER PUBLICATIONS

"Discussion on UE-to-NW Relay Implementation Aspects", Intel Corporation, 3GPP TSG RAN WG1 Meeting #80bis, R1-151442, Apr. 20-24, 2015, 9 pages, Belgrade, Serbia.

"3rd Generation Partnership Project; Technical Specification Group Radio Access Network; Evolved Universal Terrestrial Radio Access (E-UTRA); Physical layer procedures (Release 12)", 3GPP TS 36.213 V12.5.0, Mar. 2015, pp. 1-239.
"3rd Generation Partnership Project; Technical Specification Group Services and System Aspects; Proximity-based services (ProSe); Stage 2 (Release 12)", 3GPP TS 23.303 V12.4.0, Mar. 2015, 1-63.
International Search Report for PCT/JP2016/002376 dated Aug. 2, 2016 [PCT/ISA/210].
Written Opinion for PCT/JP2016/002376 dated Aug. 2, 2016 [PCT/ISA/237].
LG Electronics, "On the D2D-related information sharing between in-coverage UEs and outcoverage UEs", 3GPP TSG RAN WG1 Meeting #77; R1-142158, 3rd Generation Partnership Project (3GPP), May 18, 2014, 5 pages total.
LG Electronics, "Discussion on PD2DSCH design", 3GPP TSG RAN WG1 Meeting #78 R1-143190, Aug. 17, 2014, 5 pages total.
3rd Generation Partnership Project; Technical Specification Group Radio Access Network; Evolved Universal Terrestrial Radio Access (E-UTRA); Physical layer procedures (Release 12), 3GPP TS 36.213 V12.6.0, Jul. 3, 2015, 241 pages total.
Extended European Search Report dated Jan. 22, 2019 issued by the European Patent Office in counterpart application No. 16824016.6.

\* cited by examiner

TERMINAL, BASE STATION, AND METHOD FOR THE SAME

CROSS REFERENCE TO RELATED APPLICATIONS

This application is a National Stage of International Application No. PCT/JP2016/002376 filed May 16, 2016, claiming priority based on Japanese Patent Application No. 2015-141124 filed Jul. 15, 2015, the contents of all of which are incorporated herein by reference in their entirety.

TECHNICAL FIELD

The present disclosure relates to inter-terminal direct communication (device-to-device (D2D) communication) and, in particular, to allocation of radio resources for D2D communication.

BACKGROUND ART

A type of communication in which e a wireless terminal directly communicates with another wireless terminal without going through an infrastructure network such as a base station is called device-to-device (D2D) communication. The D2D communication includes at least one of Direct Communication and Direct Discovery. In some implementations, a plurality of wireless terminals supporting D2D communication form a D2D communication group autonomously or under the control of a network, and communicate with another wireless terminal in the formed D2D communication group.

Proximity-based services (ProSe) specified in 3GPP Release 12 is one example of the D2D communication (see, for example, Non Patent Literature 1). ProSe Direct Discovery is performed through a procedure in which a wireless terminal capable of performing ProSe (i.e., ProSe-enabled User Equipment (UE)) discovers another ProSe-enabled UE only by using the capability of a radio communication technology (e.g., Evolved Universal Terrestrial Radio Access (E-UTRA) technology) of those two UEs. ProSe Direct Discovery may be performed by three or more ProSe-enabled UEs.

ProSe Direct Communication enables establishment of a communication path between two or more ProSe-enabled UEs existing in a direct communication range after the ProSe Direct Discovery procedure is performed. Stated differently, ProSe Direct Communication enables a ProSe-enabled UE to directly communicate with another ProSe-enabled UE without going through a Public Land Mobile Network (PLMN)) including a base station (eNodeB (eNB)). ProSe Direct Communication may be performed by using a radio communication technology (i.e., E-UTRA technology) that is also used to access a base station (eNB) or by using a Wireless Local Area Network (WLAN) radio technology (i.e., IEEE 802.11 radio technology).

In 3GPP Release 12, a radio link between wireless terminals used for Direct Communication or Direct Discovery is called Sidelink (see, for example, Section 14 in Non Patent Literature 2). Sidelink transmission uses the Long Term Evolution (LTE) frame structure defined for uplink and downlink and uses a subset of uplink resources in frequency and time domains. A wireless terminal (i.e., UE) performs sidelink transmission by using Single Carrier FDMA (Frequency Division Multiple Access) (SC-FDMA), which is the same as used in uplink.

In 3GPP Release 12 ProSe, allocation of radio resources to a UE for sidelink transmission is performed by a radio access network (e.g., Evolved Universal Terrestrial Radio Access Network (E-UTRAN)). A UE that has been permitted to perform sidelink communication by a ProSe function performs ProSe Direct Discovery or ProSe Direct Communication by using radio resources allocated by a radio access network node (e.g., eNB (eNB)).

As for ProSe Direct Communication, two resource allocation modes, i.e., scheduled resource allocation and autonomous resource selection, are defined. The scheduled resource allocation and the autonomous resource selection are referred to as "sidelink transmission mode 1" and "sidelink transmission mode 2", respectively (see Section 14 in Non Patent Literature 2).

In the scheduled resource allocation for ProSe Direct Communication, when a UE desires to perform sidelink transmission, this UE requests an eNB to allocate radio resources for sidelink transmission, and the eNB allocates resources for sidelink control and data to the UE. To be specific, a UE transmits to an eNB a scheduling request to request an uplink (UL) data transmission resource (i.e., Uplink Shared Channel (UL-SCH) resource) and then transmits a Sidelink Buffer Status Report (Sidelink BSR) to the eNB by using an UL data transmission resource allocated by an uplink grant (UL grant). The eNB determines sidelink transmission resources to be allocated to the UE based on the Sidelink BSR and transmits a sidelink grant (SL grant) to the UE.

The SL grant is defined as Downlink Control Information (DCI) format 5. The SL grant (i.e., DCI format 5) contains contents such as a Resource for PSCCH, Resource block assignment and hopping allocation, and a time resource pattern index. The Resource for PSCCH indicates radio resources for a sidelink control channel (i.e., Physical Sidelink Control Channel (PSCCH)). The Resource block assignment and hopping allocation is used to determine frequency resources, i.e., a set of subcarriers (resource blocks), for transmitting a sidelink data channel (i.e., Physical Sidelink Shared Channel (PSSCH)) for sidelink data transmission. The Time resource pattern index is used to determine time resources, i.e., a set of subframes, for transmitting the PSSCH. Note that, strictly speaking, the resource block means time-frequency resources in LTE and LTE-Advanced and is a unit of resources specified by consecutive OFDM (or SC-FDMA) symbols in the time domain and consecutive subcarriers in the frequency domain. In the case of Normal cyclic prefix, one resource block includes 12 consecutive OFDM (or SC-FDMA) symbols in the time domain and 12 subcarriers in the frequency domain. That is, the Resource block assignment and hopping allocation and the Time resource pattern index designate a resource block for transmitting the PSSCH. The UE (i.e., a sidelink transmitting terminal) determines a PSCCH resource and a PSSCH resource according to the SL grant.

On the other hand, in the autonomous resource selection for ProSe Direct Communication, a UE autonomously selects resources for sidelink control (i.e., PSCCH) and data (i.e., PSSCH) from a resource pool(s) set by an eNB. The eNB may allocate a resource pool(s) for the autonomous resource selection to the UE in a System Information Block (SIB) 18. The eNB may allocate a resource pool for the autonomous resource selection to the UE in Radio Resource Control (RRC)_CONNECTED by dedicated RRC signaling. This resource pool may be usable also when the UE is in RRC_IDLE.

When direct transmission is performed on a sidelink, a UE on a transmitting side (i.e., a D2D transmitting UE) (hereinafter referred to as a transmitting terminal) transmits Scheduling Assignment information by using a portion of radio resources (i.e., resource pool) for a sidelink control channel (i.e., PSCCH). The scheduling assignment information is also referred to as Sidelink Control Information (SCI) format 0. The scheduling assignment information includes contents such as resource block assignment and hopping allocation, a time resource pattern index, and a Modulation and Coding Scheme (MCS). In the case of the above-described scheduled resource allocation, the Resource block assignment and hopping allocation and the time resource pattern index indicated by the Scheduling Assignment (i.e., SCI format 0) follow the Resource block assignment and hopping allocation and the time resource pattern index indicated by the SL grant (i.e., DCI format 5) received from the eNB.

The transmitting terminal transmits data on the PSSCH by using a radio resource according to the scheduling assignment information. A UE on a receiving side (i.e., a D2D receiving UE) (hereinafter referred to as a receiving terminal) receives the scheduling assignment information from the transmitting terminal on the PSCCH and receives the data on the PSSCH according to the received scheduling assignment information. Note that the term "transmitting terminal" just focuses on a transmission operation of a wireless terminal and does not mean a radio terminal dedicated for transmission. Similarly, the term "receiving terminal" is an expression for expressing a receiving operation of a wireless terminal and does not mean a wireless terminal dedicated for reception. That is, the transmitting terminal is able to perform a receiving operation and the receiving terminal is able to perform a transmitting operation.

Hereinafter, a sidelink control period, a resource pool for PSCCH and a resource pool for PSSCH are described. These are required to determine radio resources (i.e., subframes and resource blocks) for transmitting a PSCCH and radio resources for transmitting a PSSCH. As described earlier, the PSCCH is a sidelink physical channel to be used for transmission of sidelink control information (SCI) such as scheduling assignment information. On the other hand, the PSSCH is a sidelink physical channel to be used for user data transmission (direct transmission).

The sidelink control period is a scheduling period for sidelink (see FIG. 1). The sidelink control period is also referred to as a PSCCH period. The transmitting terminal transmits scheduling assignment information (i.e., SCI format 0) in each sidelink control period. In 3GPP Release 12, the sidelink control period is 40 ms, 60 ms, 70 ms, 80 ms, 120 ms, 140 ms, 160 ms, 240 ms, 280 ms or 320 ms. In other words, the sidelink control period is 40 subframes, 60 subframes, 70 subframes, 80 subframes, 120 subframes, 140 subframes, 160 subframes, 240 subframes, 280 subframes or 320 subframes.

Therefore, the transmitting terminal notifies the receiving terminal of the allocation of PSSCH resources in each sidelink control period, i.e., every 40 ms or more. Note that, however, the allocation of PSSCH resources is specified in units of 6, 7 or 8 subframes (6, 7 or 8 ms) by use of the time resource pattern index. Thus, in one sidelink control period, the same PSSCH resource allocation is used periodically with a period of 6, 7 or 8 subframes.

In one sidelink control period, the transmitting terminal transmits scheduling assignment information (i.e., SCI format 0) two times in two subframes out of $L_{PSCCH}$ number of subframes contained in a resource pool (subframe pool) for PSCCH. The two times of transmission is performed in two different resource blocks among $M^{PSCCH\_RP}_{RB}$ number of resource blocks contained in a resource pool (resource block pool) for PSCCH.

The resource pool for PSCCH is set to a UE by an eNB via broadcasting (SIB 18) or dedicated RRC signaling. The resource pool for PSCCH consists of $L_{PSCCH}$ number of subframes and $M^{PSCCH\_RP}_{RB}$ number of frequency domain resource blocks in a sidelink control period.

A method for specifying a resource pool for PSCCH is described hereinafter with reference to FIGS. 2 and 3. A PSCCH resource pool consists of a subframe pool and a resource block pool. FIG. 2 shows a subframe pool for PSCCH, and FIG. 3 shows a resource block pool for PSCCH.

An eNB specifies a length (P) of the sidelink control period (PSCCH period), the subframe bitmap for PSCCH and its length (N') in order to identify the subframe pool for PSCCH. The length (N') of the subframe bitmap is 4, 8, 12, 16, 30, 40 or 42 bits. The N' subframes corresponding to the subframe bitmap are the first N' subframes within the sidelink control period as shown in FIG. 2. The subframe bitmap indicates that a subframe corresponding to a bit that is set to "0" is not used for PSCCH transmission and a subframe corresponding to a bit that is set to "1" can be used for PSCCH transmission. Accordingly, the number of subframes ($L_{PSCCH}$) contained in the PSCCH resource pool in one sidelink control period is equal to the number of bits that are set to "1" within the subframe bitmap. The subframes contained in the PSCCH resource pool (i.e., subframe pool) can be represented as follows:
$(l_0^{PSCCH}, l_1^{PSCCH}, \ldots, l_{L_{PSCC}-1}^{PSCCH})$.

On the other hand, as shown in FIG. 3, the eNB specifies the index (S1) of a start Physical Resource Block (PRB), the index (S2) of an end PRB, and the number of PRBs (M) in order to identify a resource block pool for PSCCH. The resource block pool contains M number of PRBs the PRB index q of each of which is equal to or more than the start index (S1) and less than S1+M (i.e., S1<=q<S1+M) and M number of PRBs the PRB index q of each of which is more than S2−M and equal to or less than the end index (S2) (i.e., S2−M<q<=S2), i.e., the total number of PRBs is 2M. Thus, the eNB can include two PRB clusters, each containing M number of PRBs, into the resource block pool for PSCCH.

A method for specifying a resource pool for PSSCH is described hereinafter. In the case of the scheduled resource allocation (i.e., sidelink transmission mode 1), the eNB specifies a subframe pool for PSSCH via SIB 18 or dedicated signaling (RRC signaling). The sidelink control period (PSCCH period) that is associated with the PSCCH resource configuration is also associated with the PSSCH resource configuration. The UE determines the PSSCH resource pool consisting of a subframe pool as follows. Specifically, as shown in FIG. 2, in the sidelink control period (PSCCH period), subframes each having the subframe index equal to or more than $l^{PSCCH}_{PSCCH-1}+1$ belong to the subframe pool for PSSCH.

On the other hand, in the case of the autonomous resource selection (i.e., sidelink transmission mode 2), the eNB specifies a subframe pool and a resource block pool for PSSCH via SIB 18 or dedicated signaling (RRC signaling). The eNB specifies an offset ($O_2$), a subframe bitmap and its length ($N_B$) in order to specify the subframe pool.

The offset ($O_2$) indicates an offset from the subframe index $j_{begin}$ of the first subframe in the sidelink control period (i.e., PSCCH period). In this example, it is assumed that the number of subframes each having the subframe index equal to or more than $j_{begin}+O_2$ in the PSCCH period is N'.

The length ($N_B$) of the subframe bitmap is 4, 8, 12, 16, 30, 40 or 42 bits. The subframe bitmap indicates that a subframe corresponding to a bit that is set to "0" is not used for PSSCH transmission and a subframe corresponding to a bit that is set to "1" can be used for PSSCH transmission. Note that, in normal cases, the length ($N_B$) of the subframe bitmap is smaller than the total number (N') of subframes each having the subframe index equal to or more than $j_{begin}+O_2$ in the PSCCH period. Thus, the UE determines a bitmap $b_0, b_1, b_2, \ldots, b_{N'-1}$ using the following equation:

$$b_j = a_{j \bmod N_B}, \text{ for } 0 \leq j < N',$$

where $a_0, a_1, a_2, \ldots, a_{N\_B-1}$ is the bitmap with the length $N_B$ that is indicated in the PSSCH configuration by the eNB. If $b_j=1$, a subframe $l_j$ belongs to the subframe pool for PSSCH.

The resource block pool for PSSCH in the case of the autonomous resource selection (sidelink transmission mode 2) is specified in the same manner as the resource block pool for PSCCH. Specifically, in order to identify the resource block pool for PSSCH, the eNB specifies the index (S1) of a start Physical Resource Block (PRB), the index (S2) of an end PRB, and the number of PRBs (M) by the PSSCH resource configuration.

CITATION LIST

Non Patent Literature

Non-patent Literature 1: 3GPP TS 23.303 V12.4.0 (2015-03), "3rd Generation Partnership Project; Technical Specification Group Services and System Aspects; Proximity-based services (ProSe); Stage 2 (Release 12)", March 2015

Non-patent Literature 2: 3GPP TS 36.213 V12.5.0 (2015-03), "3rd Generation Partnership Project; Technical Specification Group Radio Access Network; Evolved Universal Terrestrial Radio Access (E-UTRA); Physical layer procedures (Release 12)", March 2015

SUMMARY OF INVENTION

Technical Problem

As described above, sidelink transmission of 3GPP Release 12 uses a subset of uplink resources in frequency and time domains. Thus, a UE cannot receive a sidelink signal transmitted from another UE in a subframe during sidelink transmission. This is because a signal transmitted from the UE is received by the UE itself as a high-power interference signal.

Accordingly, in a subframe in which a UE is transmitting scheduling assignment information (i.e., SCI format 0) on a PSCCH, it cannot receive scheduling assignment information (SCI format 0) transmitted from another UE. If a UE fails to receive scheduling assignment information in a certain sidelink control period (PSCCH period), it also fails in data reception (PSSCH reception) in the sidelink control period associated with this scheduling assignment information. It should be noted that the number of subframes included in the portion of radio resources for PSCCH (i.e., subframe pool for PSCCH) in which scheduling assignment information is transmitted is smaller than the number of subframes included in the portion of radio resources for data transmission (PSSCH transmission) (i.e., subframe pool for PSSCH). Accordingly, the situation where a UE cannot receive scheduling assignment information from another UE because it is transmitting scheduling assignment information (i.e., SCI format 0) on a PSCCH is likely to occur.

One of the objects attained by embodiments disclosed herein is to provide an apparatus, a method, and a program that contribute to reducing failure in reception of scheduling assignment information (SCI format 0) that is transmitted in a radio resource region for control (e.g., resource pool for PSCCH) within a periodic D2D control period (e.g., sidelink control period) and that specifies D2D transmission resources (e.g., subframes and resource blocks for PSSCH transmission).

Solution to Problem

In a first aspect, a transmitting terminal includes at least one wireless transceiver and at least one processor. The at least one processor is coupled to the at least one wireless transceiver and configured to perform data transmission to another wireless terminal without going through a base station in accordance with device-to-device (D2D) control periods that occur periodically. Each of the D2D control periods includes a first subframe pool consisting of a plurality of subframes usable for transmission of D2D control information and a second subframe pool consisting of a plurality of subframes usable for the data transmission in accordance with the D2D control information. The at least one processor is configured to transmit first D2D control information in one or more subframes within the first subframe pool within a first D2D control period and perform the data transmission in accordance with the first D2D control information in one or more subframes within the second subframe pool within the first D2D control period. The first D2D control information contains a first information element for identifying the one or more subframes within the second subframe pool within the first D2D control period. The first D2D control information further contains a second information element indicating whether the first D2D control information is valid in at least one D2D control period occurring after the first D2D control period.

In a second aspect, a method in a transmitting terminal includes performing data transmission to a receiving terminal without going through a base station in accordance with device-to-device (D2D) control periods that occur periodically. Each of the D2D control periods includes a first subframe pool consisting of a plurality of subframes usable for transmission of D2D control information and a second subframe pool consisting of a plurality of subframes usable for the data transmission in accordance with the D2D control information. The performing the data transmission includes transmitting first D2D control information in one or more subframes within the first subframe pool within a first D2D control period and performing the data transmission in accordance with the first D2D control information in one or more subframes within the second subframe pool within the first D2D control period. The first D2D control information contains a first information element for identifying the one or more subframes within the second subframe pool within the first D2D control period. The first D2D control information further contains a second information element indicating whether the first D2D control information is valid in at least one D2D control period occurring after the first D2D control period.

In a third aspect, a receiving terminal includes at least one wireless transceiver and at least one processor. The at least one processor is coupled to the at least one wireless transceiver and configured to perform data reception from a transmitting terminal without going through a base station in accordance with device-to-device (D2D) control periods that occur periodically. Each of the D2D control periods includes a first subframe pool consisting of a plurality of subframes usable for transmission of D2D control information and a second subframe pool consisting of a plurality of subframes usable for the data reception in accordance with the D2D control information. The at least one processor is configured to receive first D2D control information in one or more subframes within the first subframe pool within a first D2D control period and perform the data reception in accordance with the first D2D control information in one or more subframes within the second subframe pool within the first D2D control period. The first D2D control information contains a first information element for identifying the one or more subframes within the second subframe pool within the first D2D control period. The first D2D control information further contains a second information element indicating whether the first D2D control information is valid in at least one D2D control period occurring after the first D2D control period.

In a fourth aspect, a method in a receiving terminal includes performing data reception from a transmitting terminal without going through a base station in accordance with device-to-device (D2D) control periods that occur periodically. Each of the D2D control periods includes a first subframe pool consisting of a plurality of subframes usable for transmission of D2D control information and a second subframe pool consisting of a plurality of subframes usable for the data reception in accordance with the D2D control information. The performing the data reception includes receiving first D2D control information in one or more subframes within the first subframe pool within a first D2D control period and performing the data reception in accordance with the first D2D control information in one or more subframes within the second subframe pool within the first D2D control period. The first D2D control information contains a first information element for identifying the one or more subframes within the second subframe pool within the first D2D control period. The first D2D control information further contains a second information element indicating whether the first D2D control information is valid in at least one D2D control period occurring after the first D2D control period.

In a fifth aspect, a base station includes a wireless transceiver configured to communicate with a plurality of wireless terminals in a cell, and at least one processor. The at least one processor is configured to control data transmission. The data transmission is performed from a first wireless terminal to a second wireless terminal without going through the base station in accordance with device-to-device (D2D) control periods that occur periodically. Each of the D2D control periods includes a first subframe pool consisting of a plurality of subframes usable for transmission of D2D control information and a second subframe pool consisting of a plurality of subframes usable for the data transmission in accordance with the D2D control information. The at least one processor is configured to transmit, to the first wireless terminal, a D2D grant message indicating radio resource allocation for transmission of the D2D control information and the data transmission in a first D2D control period and further indicating that the radio resource allocation is valid also in at least one D2D control period occurring after the first D2D control period.

In a sixth aspect, a method in a base station includes controlling data transmission. The data transmission is performed from a first wireless terminal to a second wireless terminal without going through the base station in accordance with device-to-device (D2D) control periods that occur periodically. Each of the D2D control periods includes a first subframe pool consisting of a plurality of subframes usable for transmission of D2D control information and a second subframe pool consisting of a plurality of subframes usable for the data transmission in accordance with the D2D control information. The controlling includes transmitting, to the first wireless terminal, a D2D grant message indicating radio resource allocation for transmission of the D2D control information and the data transmission in a first D2D control period and further indicating that the radio resource allocation is valid also in at least one D2D control period occurring after the first D2D control period.

In a seventh aspect, a program includes a set of instructions (software codes) that, when loaded into a computer, causes the computer to perform the method according to the above-described second, fourth or sixth aspect.

Advantageous Effects of Invention

According to the above-described aspects, it is possible to provide an apparatus, a method, and a program that contribute to reducing failure in reception of scheduling assignment information (SCI format 0) that is transmitted in a radio resource region for control (e.g., resource pool for PSCCH) within a periodic D2D control period (e.g., sidelink control period) and that specifies D2D transmission resources (e.g., subframes and resource blocks for PSSCH transmission).

DESCRIPTION OF EMBODIMENTS

Specific embodiments will be described hereinafter in detail with reference to the drawings. The same or corresponding elements are denoted by the same symbols throughout the drawings, and duplicated explanations are omitted as necessary for the sake of clarity.

The following embodiments will be described on the assumption that they are implemented to improve ProSe specified in 3GPP Release 12 (LTE-Advanced). However, these embodiments are not limited to the LTE-Advanced and its improvements and may also be applied to D2D communication in other mobile communication networks or systems.

First Embodiment

Figure 1:
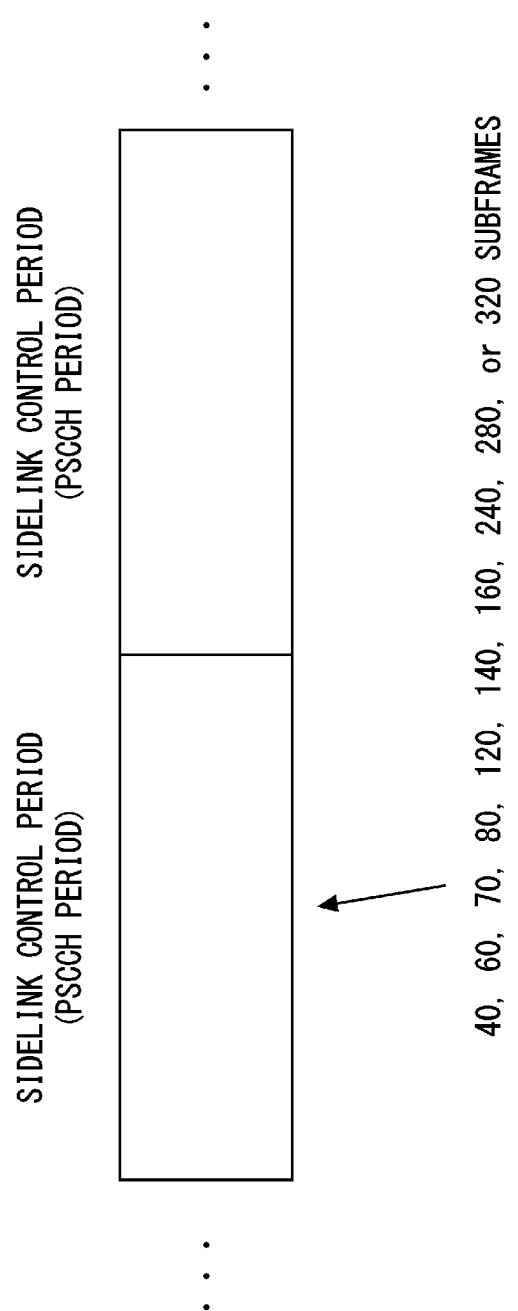
FIG. 1 is a view showing a sidelink control period (PSCCH period).
Figure 2:
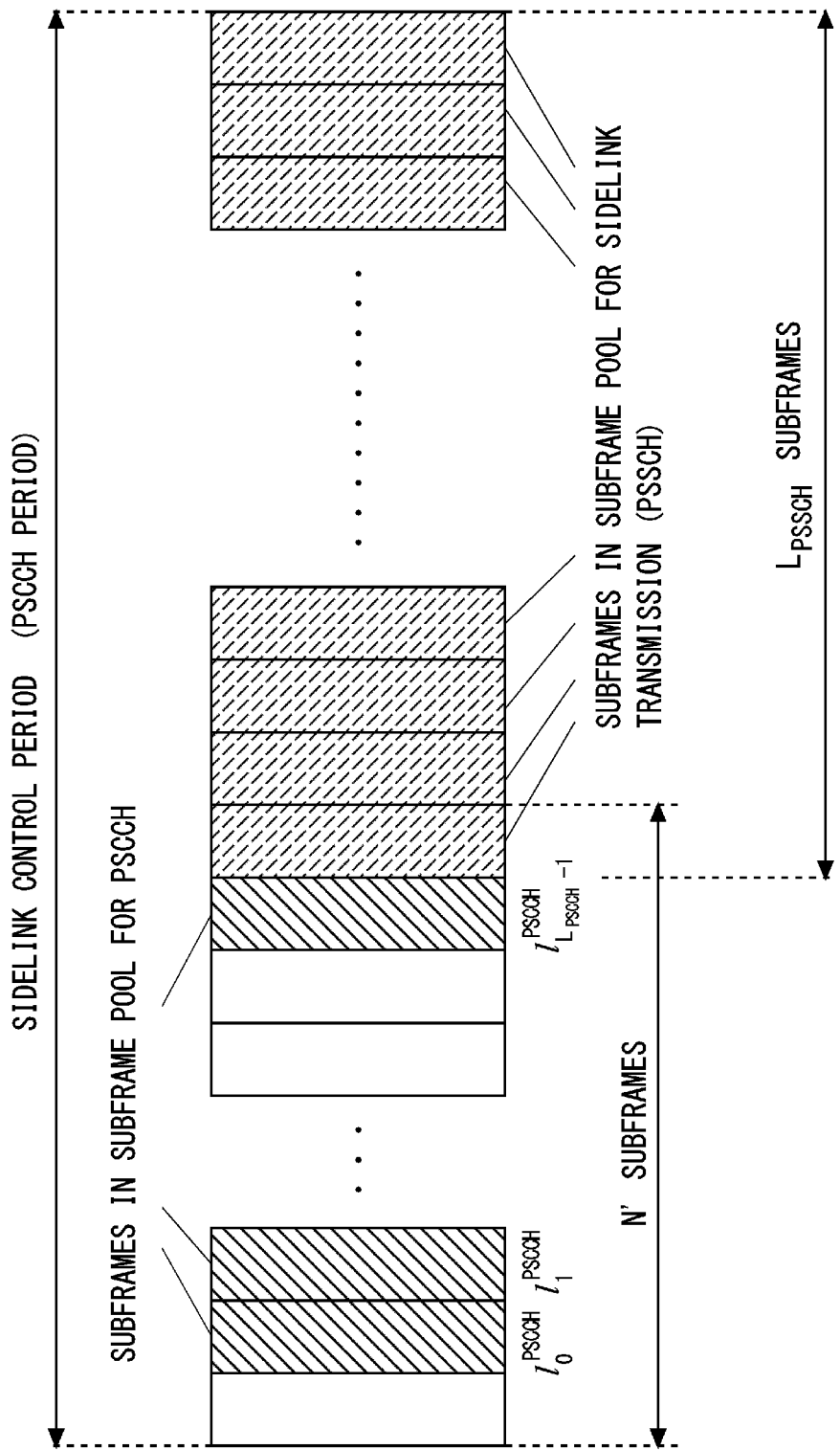
FIG. 2 is a view showing an example of a PSCCH subframe pool and a PSSCH subframe pool in a sidelink control period.
Figure 3:
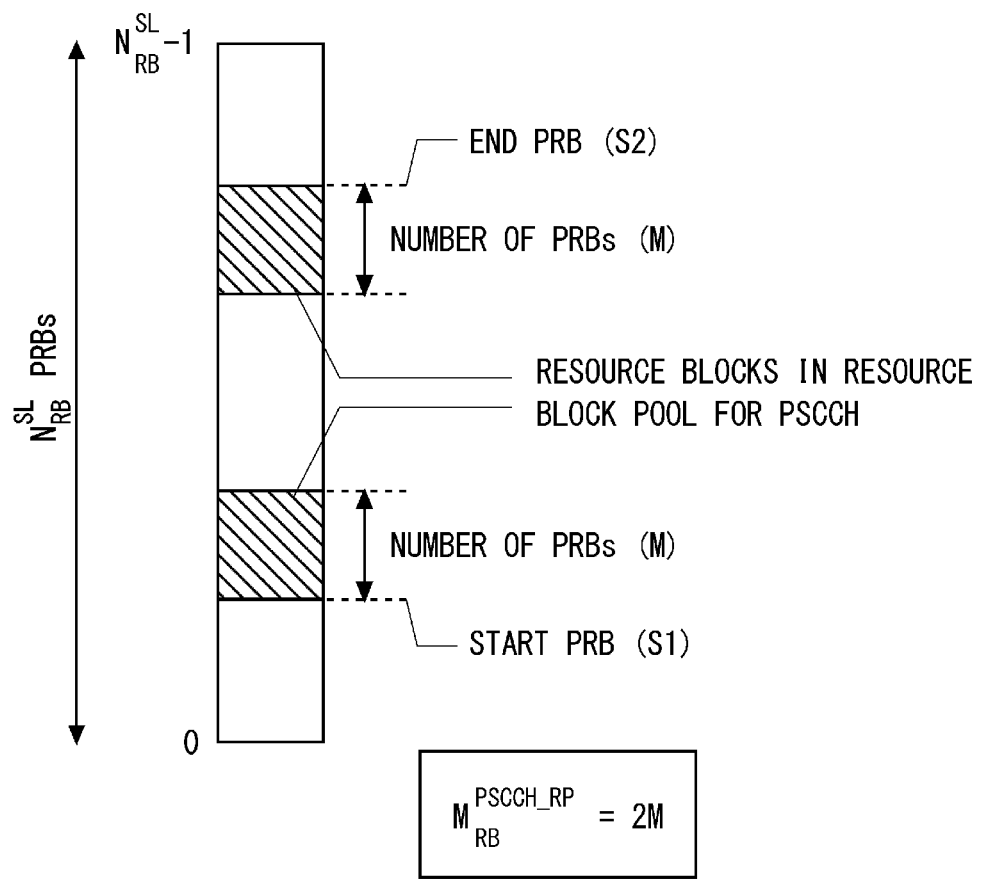
FIG. 3 is a view showing an example of a PSCCH resource block pool in a sidelink control period.
Figure 4:
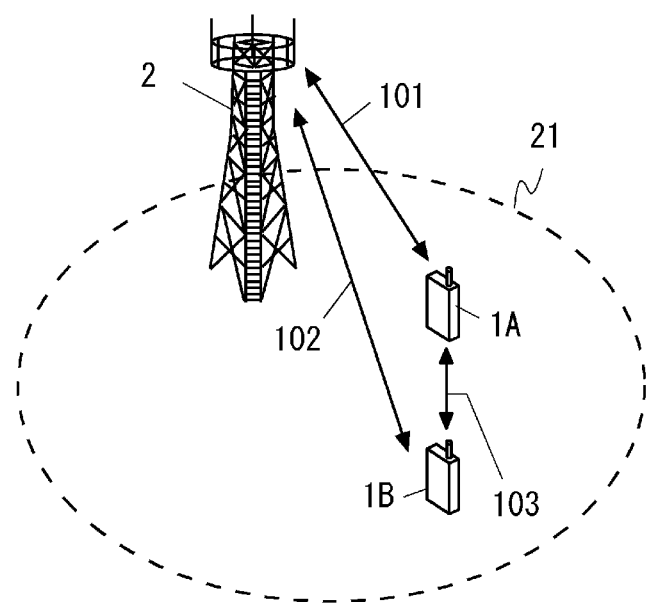
FIG. 4 is a view showing a configuration example of a wireless communication system according to some embodiments.

FIG. 4 shows a configuration example of a wireless communication system according to some embodiments including this embodiment. Each of wireless terminals (UEs) 1A and 1B includes at least one wireless transceiver and is configured to perform cellular communication (101 or 102) with a base station (eNB) 2 and perform D2D communication on a device-to-device direct interface (e.g., PC5 interface or sidelink) 103. This D2D communication includes at least Direct Communication (ProSe Direct Communication) and may further include Direct Discovery (e.g., ProSe Direct Discovery). The eNB 2 manages a cell 21 and is able to perform cellular communication (101 or 102) with each of the plurality of UEs 1 by using a cellular communication technology (e.g., Evolved Universal Terrestrial Radio Access (E-UTRA) technology). Although the example of FIG. 4 indicates an arrangement where the UEs 1A and 1B are located in the same cell 21 for simplification of description, such arrangement is just one example. For example, the UE 1A may be located in one of two cells that are adjacent to each other and are managed by different eNBs 2, and the UE 1B may be located in the other one of the two cells. Alternatively, at least one of the UE 1A and the UE 1B may be located outside the coverage of one or more eNBs 2.

The following provides descriptions for PSCCH and PSSCH transmissions on sidelink according to this embodiment. A transmitting terminal (e.g., UE 1A) is configured to perform data transmission to another wireless terminal (i.e., receiving terminal (e.g., UE 1B)) without going through the eNB 2 in accordance with D2D control periods that occur periodically (i.e., sidelink control periods (PSCCH periods)). As described earlier, each sidelink control period includes a subframe pool for PSCCH (first subframe pool) and a subframe pool for PSSCH (second subframe pool). The subframe pool for PSCCH consists of $L_{PSCCH}$ subframes that are usable for transmission of sidelink control information (SCI) containing scheduling assignment information (i.e., SCI format 0). On the other hand, the subframe pool for PSSCH consists of $L_{PSSCH}$ subframes that are usable for data transmission (i.e., PSSCH transmission) in accordance with the scheduling assignment information (i.e., SCI format 0).

Specifically, the transmitting terminal (e.g., UE 1A) transmits sidelink control information (D2D control information) in one or more subframes (e.g., two subframes) within the PSCCH subframe pool within the j-th sidelink control period. Further, the transmitting terminal (e.g., UE 1A) performs data transmission (PSSCH transmission) in accordance with the sidelink control information in one or more subframes within the PSSCH subframe pool within the j-th sidelink control period. The sidelink control information that is transmitted within the j-th sidelink control period contains a first information element (i.e., scheduling assignment information (SCI format 0)) for identifying the one or more subframes within the PSSCH subframe pool within the j-th sidelink control period. In addition, the sidelink control information that is transmitted in the j-th sidelink control period contains a second information element indicating whether radio resource allocation for the data transmission (PSSCH transmission) indicated by this sidelink control information continues to be valid in at least one of the (j+1)th and subsequent sidelink control periods.

The transmitting terminal (e.g., UE 1A) may be configured to perform the data transmission on the PSSCH without transmitting new sidelink control information (i.e., scheduling assignment information (SCI format 0)) in at least one of the (j+1)th and subsequent sidelink control periods in which the radio resource allocation for the data transmission in the j-th sidelink control period continues to be valid. Meanwhile, the receiving terminal (e.g., UE 1B) may be configured to perform the data reception on the PSSCH without receiving new sidelink control information (i.e., scheduling assignment information) in the (j+1)th and subsequent sidelink control periods when the radio resource allocation for the data transmission in the j-th sidelink control period continues to be valid in at least one of the (j+1)th and subsequent sidelink control periods.

It is thus possible to reduce the probability that the transmitting terminal fails to receive the sidelink control information from another UE 1 in at least one of the (j+1)th and subsequent sidelink control periods. Further, as a result of the PSCCH transmission according to this embodiment, it is possible to reduce the number of PSCCH transmissions compared to the case of transmitting sidelink control information (i.e., scheduling assignment information) every sidelink control period. Accordingly, it is possible to reduce the probability of collisions where PSCCH transmissions by a plurality of sidelink transmitting terminals located in close proximity to each other are performed in the same radio resources.

In some implementations, the second information element may specify the length of the at least one of the (j+1)th and subsequent sidelink control periods (i.e., at least one sidelink control period in which the radio resource allocation for the data transmission in the j-th sidelink control period continues to be valid). For example, the second information element may specify the number of sidelink control periods during which the sidelink control information (i.e., scheduling assignment information (SCI format 0)) transmitted in the j-th sidelink control period is valid.

The transmitting terminal may autonomously determine the number of sidelink control periods during which the radio resource allocation for the data transmission in the j-th sidelink control period continues to be valid (hereinafter referred to as "the number of valid sidelink control periods"). Alternatively, the eNB 2 may set the number of valid sidelink control periods for radio resource allocation to the transmitting terminal. For example, in the case of the scheduled resource allocation (i.e., sidelink transmission mode 1), the eNB 2 may notify the transmitting terminal of the number of valid sidelink control periods for radio resource allocation by using a sidelink scheduling grant (DCI format 5). In the case of the autonomous resource selection (i.e., sidelink transmission mode 2), the eNB 2 may notify the transmitting terminal of the number of valid sidelink control periods for radio resource allocation by using a PSCCH resource configuration or a PSSCH resource configuration via SIB 18 or RRC signaling.

For example, the transmitting terminal may determine the number of valid sidelink control periods for radio resource allocation in accordance with the amount of data in a data buffer to be transmitted on sidelink. Specifically, the transmitting terminal may determine the number of valid sidelink control periods corresponding to the PSSCH resources needed to transmit the pending data. As a result of this, it is possible to appropriately reduce the number of transmissions of the sidelink control information (scheduling assignment information (SCI format 0)) on the PSCCH.

For example, the transmitting terminal may determine the number of valid sidelink control periods for radio resource allocation in accordance with a delay requirement needed by an application (i.e., application program). The delay requirement may be at least one of: the maximum delay; the average delay; and the priority related to delay guarantee. The transmitting terminal may increase the number of valid sidelink control periods when an application needs a strict delay requirement (i.e., low delay) compared to when it does not. This can suppress failure in reception of the sidelink control information and failure in the data transmission for a long period of time, thereby contributing to achieving the strict delay requirement (i.e., low delay) needed by the application.

For example, the eNB 2 may set, to the transmitting terminal, the number of valid sidelink control periods according to the number of sidelink transmissions (or the number of sidelink transmission terminals) in the cell 21. For example, the eNB 2 may increase the number of valid sidelink control periods as the number of sidelink transmission (the number of sidelink transmission terminals) in the cell 21 increases. This can reduce the number of occurrence of PSCCH transmissions when the number of sidelink transmissions performed (or the number of sidelink transmission terminals) in the cell 21 is large. It is thus possible to reduce the probability of collisions where a plurality of PSCCH transmissions by a plurality of sidelink transmitting terminals located in close proximity to each other are performed in the same radio resources.

Alternatively, in some implementations, the second information element may indicate whether the radio resource allocation for data transmission in the j-th sidelink control period is maintained or not. The second information element may be flag information indicating whether or not the radio resource allocation is maintained. For example, the second information element may be 1-bit flag information. The flag with a value of "1" may indicate that the radio resource allocation for data transmission in the j-th sidelink control period is valid also in the (j+1)th and subsequent sidelink control periods. On the other hand, the flag with a value of "0" may indicate that the radio resource allocation for data transmission in the j-th sidelink control period is valid only in the j-th sidelink control period.

Figure 5:
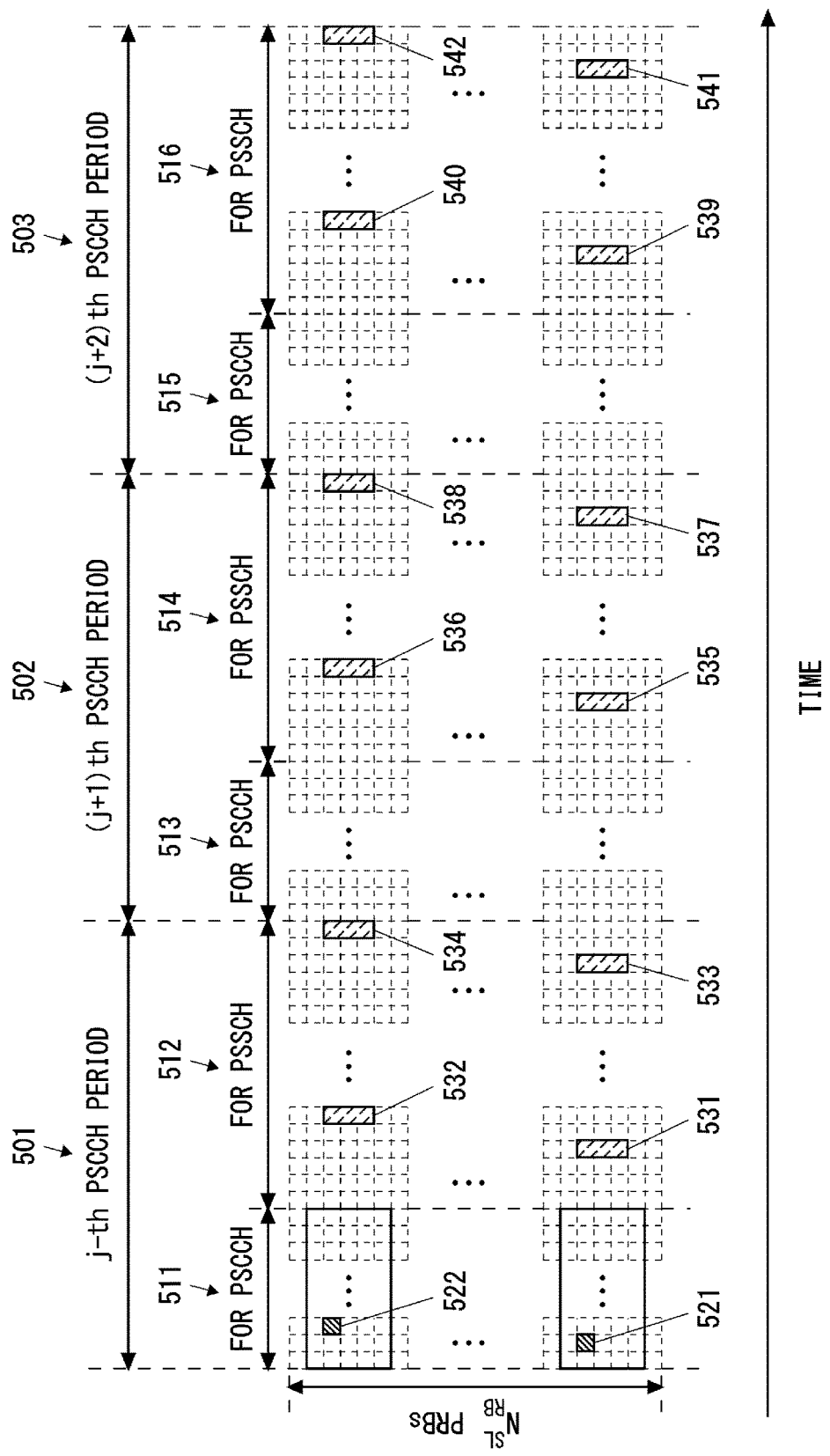
FIG. 5 is a view illustrating transmission of scheduling assignment information (PSCCH) and data (PSSCH) on sidelink by a wireless terminal (transmitting terminal) according to a first embodiment.

FIG. 5 is a view showing one example of transmission of PSCCH and PSSCH according to this embodiment. In the example of FIG. 5, the transmitting terminal (e.g., UE 1A) transmits sidelink control information (522 and 523) on the PSCCH in two subframes within the PSCCH subframe pool 511 within the j-th sidelink control period (PSCCH period) 501. The sidelink control information 522 and 523 transmitted in the j-th sidelink control period 501 contains scheduling assignment information (i.e., SCI format 0) and further indicates that this scheduling assignment information is valid also in the (j+1)th sidelink control period 502 and subsequent sidelink control periods.

The transmitting terminal (e.g., UE 1A) performs data transmissions (PSSCH transmissions) 531 to 534 in accordance with the sidelink control information 522 and 523 in a plurality of subframes within the PSSCH subframe pool 512 within the j-th sidelink control period 501. Further, the transmitting terminal (e.g., UE 1A) performs data transmissions (PSSCH transmissions) 535 to 538 in the PSSCH subframe pool 514 within the (j+1)th sidelink control period 502 without transmitting sidelink control information in the PSCCH subframe pool 513 within the (j+1)th sidelink control period 502. The data transmissions (PSSCH transmissions) 535 to 538 are performed in accordance with the sidelink control information 522 and 523 transmitted previously in the j-th sidelink control period 501. Likewise, the transmitting terminal (e.g., UE 1A) performs data transmissions (PSSCH transmissions) 539 to 542 in the PSSCH subframe pool 516 within the (j+2)th sidelink control period 503 without transmitting sidelink control information in the PSCCH subframe pool 515 within the (j+2)th sidelink control period 503. The data transmissions (PSSCH transmissions) 539 to 542 are performed in accordance with the sidelink control information 522 and 523 transmitted previously in the j-th sidelink control period 501.

Figure 6:
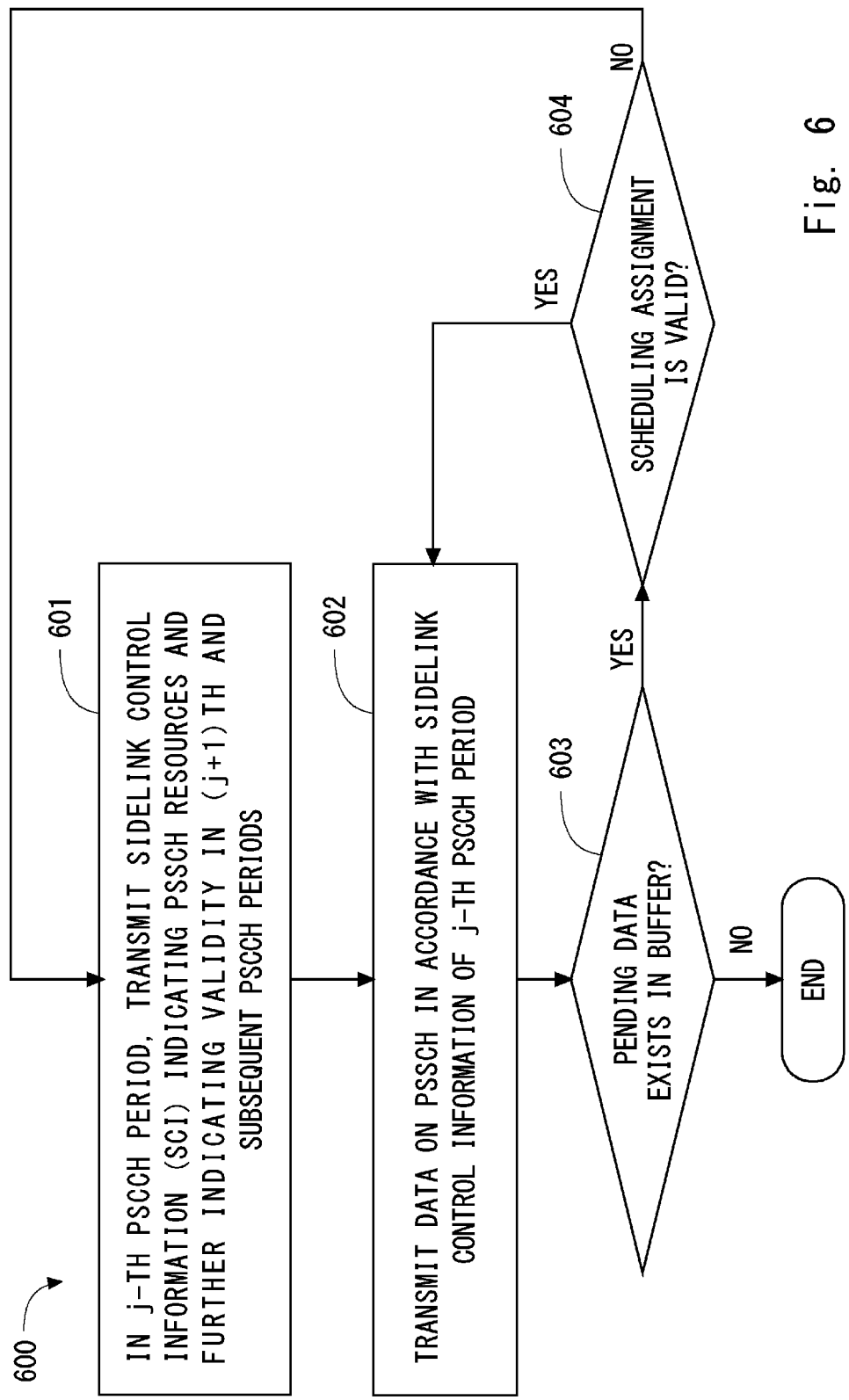
FIG. 6 is a flowchart showing an example of an operation of a wireless terminal (transmitting terminal) according to the first embodiment.

FIG. 6 is a flowchart showing one example of an operation (process 600) of the transmitting terminal (e.g., UE 1A) according to this embodiment. In Block 601, in the j-th sidelink control period (PSCCH period), the transmitting terminal transmits, to the receiving terminal (e.g., UE 1B), sidelink control information (SCI) indicating PSSCH resources and further indicating the validity of the PSSCH resource allocation in the (j+1)th and subsequent sidelink control periods (i.e., PSCCH periods). In Block 602, in the j-th sidelink control period (PSCCH period), the transmitting terminal transmits data on the PSSCH in accordance with the sidelink control information of the j-th sidelink control period.

In Block 603, the transmitting terminal determines whether pending data to be transmitted on sidelink exists in a buffer or not. When the pending data exists in a buffer (YES in Block 603), the transmitting terminal determines whether it has valid scheduling assignment for a receiving terminal of the pending data (Block 604). When it has the valid scheduling assignment (YES in Block 604), the transmitting terminal transmits data on the PSSCH in the (j+1)th sidelink control period or a subsequent sidelink control period (i.e., PSCCH period) in accordance with the sidelink control information of the j-th sidelink control period. On the other hand, when it does not have the valid scheduling assignment (No in Block 604), the transmitting terminal returns to the process in Block 601 to transmit new sidelink control information (i.e., scheduling assignment information (SCI format 0)).

Figure 7:
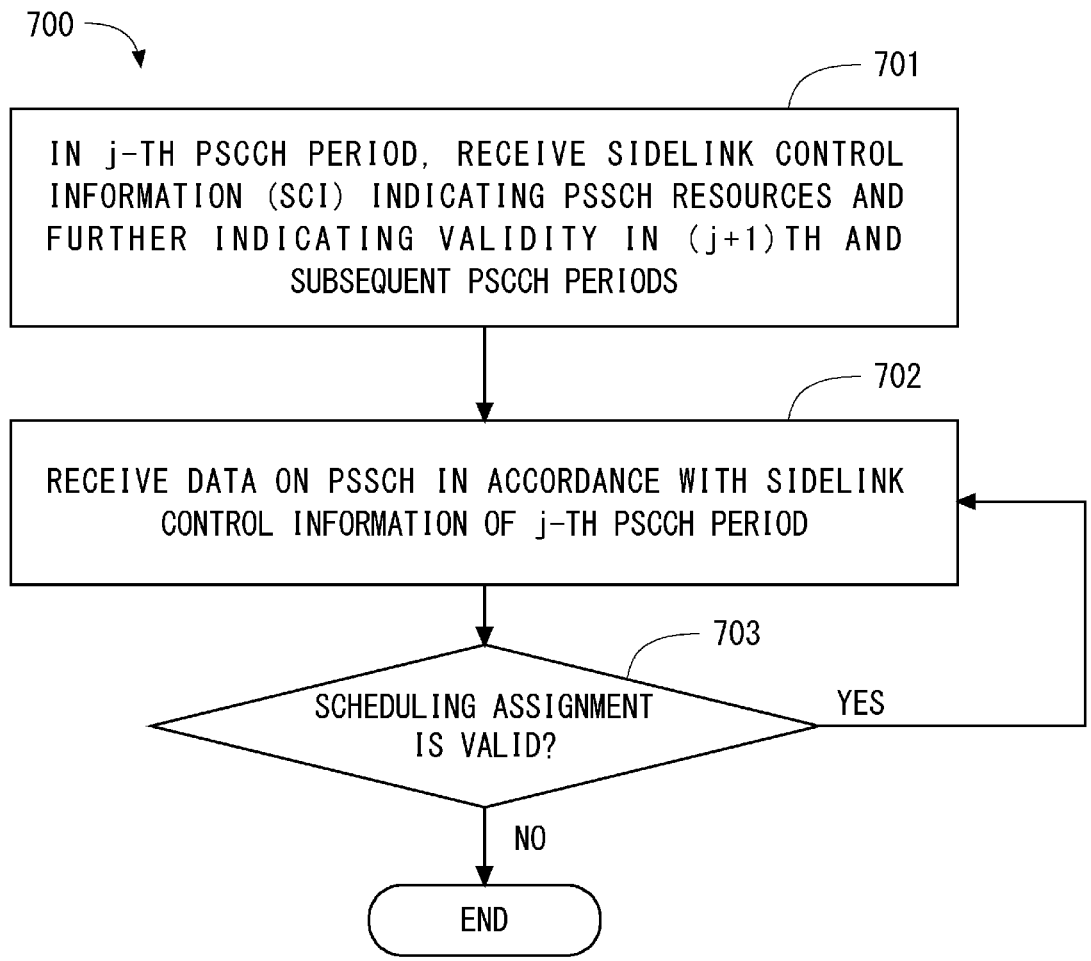
FIG. 7 is a flowchart showing an example of an operation of a wireless terminal (receiving terminal) according to the first embodiment.

FIG. 7 is a flowchart showing one example of an operation (process 700) of the receiving terminal (e.g., UE 1B) according to this embodiment. In Block 701, in the j-th sidelink control period (i.e., PSCCH period), the receiving terminal receives, from the transmitting terminal (e.g., UE 1A), sidelink control information (SCI) indicating PSSCH resources and further indicating the validity of PSSCH resource allocation in the (j+1)th and subsequent sidelink control periods (i.e., PSCCH periods). In Block 702, in the j-th sidelink control period (PSCCH period), the receiving terminal receives data on the PSSCH in accordance with the sidelink control information of the j-th sidelink control period.

In Block 703, the receiving terminal determines whether it has valid scheduling assignment or not. When it has the valid scheduling assignment (YES in Block 703), the receiving terminal receives data on the PSSCH in the (j+1)th sidelink control period or a subsequent sidelink control period (i.e., PSCCH period) in accordance with the sidelink control information of the j-th sidelink control period.

Figure 8:
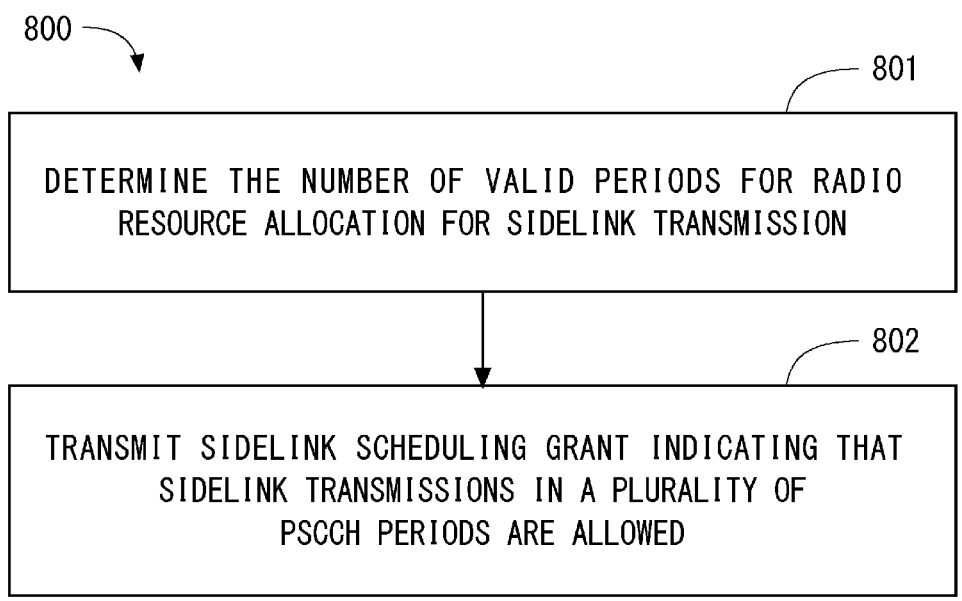
FIG. 8 is a flowchart showing an example of an operation of a base station according to the first embodiment.

FIG. 8 is a flowchart showing one example of an operation (process 700) of the eNB 2 according to this embodiment. As described earlier, the eNB 2 may set, to the transmitting terminal, the number of valid sidelink control periods for radio resource allocation. FIG. 8 shows the case of the scheduled resource allocation (i.e., sidelink transmission mode 1). In Block 801, the eNB 2 determines the number of valid sidelink control periods for radio resource allocation for sidelink transmission. In Block 802, the eNB 2 transmits, to the UE 1 (transmitting terminal), a sidelink scheduling grant indicating that sidelink transmissions in a plurality of sidelink control periods (i.e., PSCCH periods) are allowed. Specifically, the sidelink scheduling grant indicates PSCCH transmission resource allocation, PSSCH transmission resource allocation, and the number of sidelink control periods during which the PSSCH transmission resource allocation is valid.

Second Embodiment

This embodiment provides a modified example of sidelink transmission described in the first embodiment. A configuration example of a wireless communication system according to this embodiment is the same as that shown in FIG. 4. In this embodiment, a procedure to disable (or cancel) PSSCH resource allocation over a plurality of sidelink control periods is described.

In some implementations, the transmitting terminal (e.g., UE 1A) may be configured to transmit to the receiving terminal (e.g., UE 1B), in any of the (j+1)th and subsequent sidelink control periods, sidelink control information that indicates disabling of the radio resource allocation for the (j+1)th data transmission or a subsequent data transmission (i.e., PSSCH transmission) based on the sidelink control information (scheduling assignment information) transmitted previously in the j-th sidelink control period. Stated differently, the transmitting terminal may transmit, in any of the (j+1)th and subsequent sidelink control periods, sidelink control information indicating disabling (or cancellation) of scheduling assignment, in order to disable (or cancel) the PSSCH scheduling assignment (SCI format 0) in the j-th sidelink control period that has been valid over a plurality of sidelink control periods.

As the sidelink control information indicating disabling (or cancellation) of the scheduling assignment, a reserved value (e.g., a value such as 11111111 in the case of 8 bits) of the number of valid periods for scheduling assignment may be used. Alternatively, the sidelink control information indicating disabling (or cancellation) of the scheduling assignment may contain a flag indicating disabling of the scheduling assignment.

Note that a plurality of scheduling assignments may be made valid between the transmitting terminal and the receiving terminal. In this case, the receiving terminal may disable all of the valid scheduling assignments in response to the information indicating disabling (or cancellation) received from the transmitting terminal. Alternatively, the transmitting terminal may transmit, to the receiving terminal, an identifier(s) indicating a scheduling assignment(s) to be disabled among the plurality of valid scheduling assignments.

Alternatively or additionally, in some implementations, the receiving terminal (e.g., UE 1B) may autonomously disable (or cancel) the scheduling assignment that has been valid over a plurality of sidelink control periods. For example, the receiving terminal (e.g., UE 1B) may disable the scheduling assignment (i.e., PSSCH resource allocation) enabled in the j-th sidelink control period when data reception on the PSSCH from the transmitting terminal (e.g., UE 1A) does not occur for a specified period of time in the (j+1)th sidelink control period or a subsequent sidelink control period.

In the case where the scheduling assignment (i.e., PSSCH resource allocation) is enabled over a plurality of sidelink control periods), there is a possibility that the receiving terminal attempts to receive data on the PSSCH in each sidelink control period within the valid sidelink control period in spite of that data transmission on the PSSCH does not occur in the (j+1)th sidelink control period or a subsequent sidelink control period due to the absence of pending data to be transmitted in a buffer of the transmitting terminal (that is, sidelink transmission has completed). Such an unnecessary receiving operation causes unnecessary power consumption in the receiving terminal or reduction of transmission opportunities. According to the scheduling assignment disabling procedure described in this embodiment, it is possible to suppress such an adverse effect.

Figure 9:
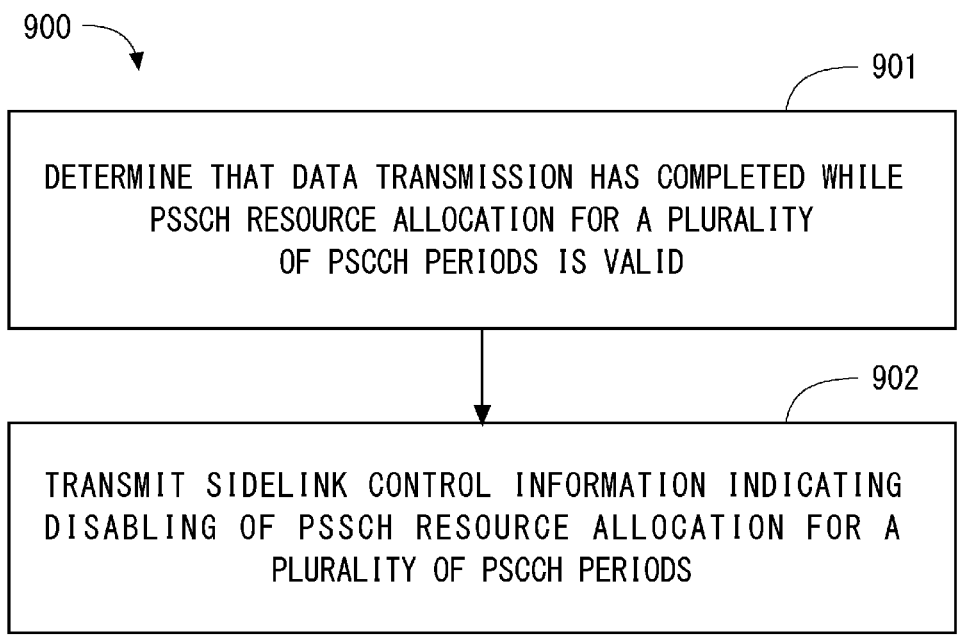
FIG. 9 is a flowchart showing an example of an operation of a wireless terminal (transmitting terminal) according to a second embodiment.

FIG. 9 is a flowchart showing an example of an operation (process 900) of the transmitting terminal according to this embodiment. In Block 901, the transmitting terminal determines that data transmission has completed while PSSCH resource allocation for a plurality of sidelink control periods (i.e., PSCCH periods) is valid. In Block 902, the transmitting terminal transmits, to the receiving terminal, sidelink control information indicating disabling of the PSSCH resource allocation for the plurality of sidelink control periods (i.e., PSCCH periods).

Figure 10:
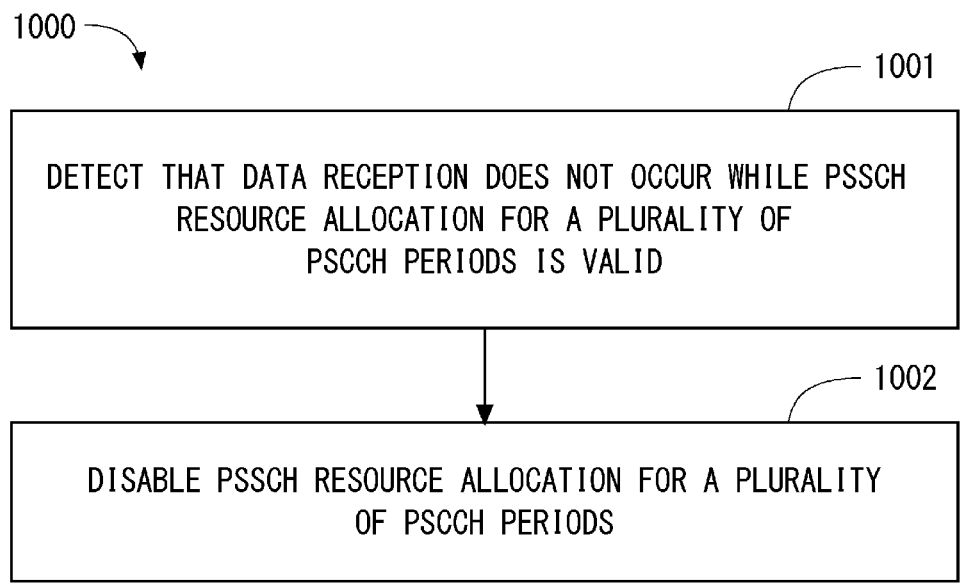
FIG. 10 is a flowchart showing an example of an operation of a wireless terminal (receiving terminal) according to the second embodiment.

FIG. 10 is a flowchart showing an example of an operation (process 1000) of a receiving terminal according to this embodiment. In Block 1001, the receiving terminal detects that data reception on the PSSCH from the transmitting terminal does not occur for a specified period of time while PSSCH resource allocation for a plurality of sidelink control periods (i.e., PSCCH periods) is valid. In Block 1002, the receiving terminal autonomously disables the PSSCH resource allocation for the plurality of sidelink control periods (i.e., PSCCH periods).

Third Embodiment

This embodiment provides a modified example of sidelink transmission described in the first embodiment. A configuration example of a wireless communication system according to this embodiment is the same as that shown in FIG. 4. In this embodiment, the transmitting terminal (e.g., UE 1A) is configured to impose, on the transmitting terminal itself, a restriction regarding PSSCH resource allocation over a plurality of sidelink control periods, autonomously or under control of the eNB 2. In this embodiment, an example in which a restriction is imposed individually on a specific UE 1 or on a specific UE group in the cell 21 is described.

In some implementations, the transmitting terminal may impose, on the transmitting terminal itself, a restriction regarding PSSCH resource allocation over a plurality of sidelink control periods, autonomously or under control of the eNB 2, when it is assumed to be located at a cell boundary between the cell 21 (i.e., serving cell) of the eNB 2 and an adjacent cell. In this case, the restriction may indicate that the continuous enabling of PSSCH resource allocation over a plurality of sidelink control periods is not allowed. Alternatively, the restriction may set the upper limit value to the number of sidelink control periods during which PSSCH resource allocation is valid (i.e., the number of valid sidelink control periods).

The fact that the transmitting terminal is located at the cell boundary may be determined by any one or any combination of the following conditions (a) to (d):
(a) The reception quality (e.g., Reference Signal Received Power (RSRP) or Reference Signal Received Quality (RSRQ)) of a downlink signal of the serving cell 21 is equal to or less than a specified value;
(b) The reception quality of a downlink signal of an adjacent cell is equal to or higher than a specified value;
(c) The distance from the eNB 2 of the serving cell 21 is equal to or greater than a specified value; and
(d) The distance from the eNB of the adjacent cell is equal to or smaller than a specified value.

In the case where the transmitting terminal is assumed to be located at the cell boundary between the cell 21 (i.e., serving cell) of the eNB 2 and the adjacent cell, there is a possibility that the transmitting terminal causes interference to an UE or the eNB of the adjacent cell. Thus, stated differently, the transmitting terminal may impose, on the transmitting terminal itself, a restriction regarding PSSCH resource allocation over a plurality of sidelink control periods, autonomously or under control of the eNB 2, when there is a possibility that it causes interference to an UE or an eNB of an adjacent cell.

Figure 11:
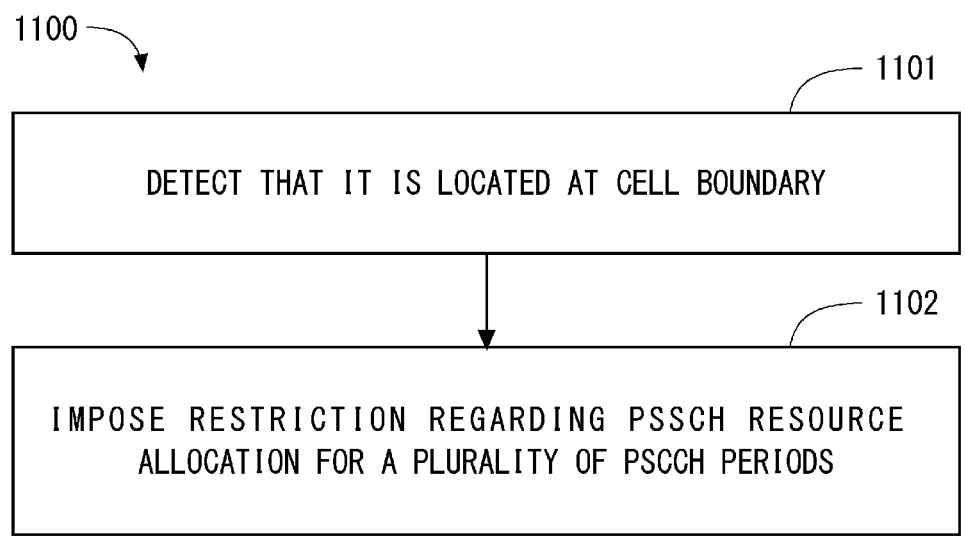
FIG. 11 is a flowchart showing an example of an operation of a wireless terminal (transmitting terminal) according to a third embodiment.

FIG. 11 is a flowchart showing an example of an operation (process 1100) of a transmitting terminal according to this embodiment. In Block 1101, the transmitting terminal detects that it is located at the cell boundary. In Block 1102, the transmitting terminal imposes a restriction regarding PSSCH resource allocation for a plurality of sidelink control periods (i.e., PSCCH periods).

Sidelink transmission performed by the transmitting terminal located at the cell boundary may cause interference to sidelink transmission or uplink transmission performed in an adjacent cell. In this embodiment, a restriction regarding PSSCH resource allocation over a plurality of sidelink control periods can be set to the transmitting terminal, and it is thus possible to avoid the situation where the transmitting terminal continuously causes interference to sidelink transmission or uplink transmission performed in an adjacent cell.

Fourth Embodiment

This embodiment provides a modified example of sidelink transmission described in the first embodiment. A configuration example of a wireless communication system according to this embodiment is the same as that shown in FIG. 4. In this embodiment, the transmitting terminal (e.g., UE 1A) is configured to impose, on the transmitting terminal itself, a restriction regarding PSSCH resource allocation over a plurality of sidelink control periods under control of the eNB 2. In this embodiment, an example where a restriction is imposed individually to a specific UE 1 or a specific UE group in the cell 21 is described.

In some implementations, when the number of sidelink transmissions (or the number of sidelink transmission terminals) in the cell 21 exceeds a specified value, the eNB 2 may impose, on a part or all of the sidelink transmitting terminals in the cell 21, a restriction regarding PSSCH resource allocation over a plurality of sidelink control periods. In this case, the restriction may set the lower limit value (no less than 2) to the number of sidelink control periods during which PSSCH resource allocation is valid (i.e., the number of valid sidelink control periods). As a result of this, the eNB 2 can reduce the number of occurrence of PSCCH transmissions when the number of sidelink transmissions performed (or the number of sidelink transmission terminals) in the cell 21 is large. It is thus possible to reduce the usage rate of the PSCCH resource pool. Accordingly, it is possible to reduce the probability of collisions where PSCCH transmissions by a plurality of sidelink transmitting terminals located in close proximity to each other are performed in the same radio resources.

Figure 12:
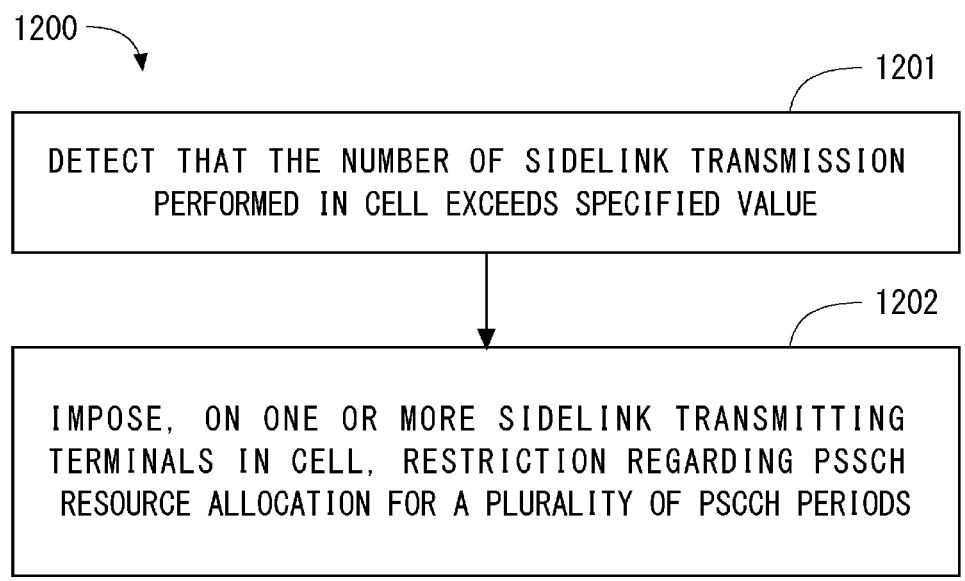
FIG. 12 is a flowchart showing an example of an operation of a base station according to a fourth embodiment.

FIG. 12 is a flowchart showing an example of an operation (process 1200) of the eNB 2 according to this embodiment. In Block 1201, the eNB 2 detects that the number of sidelink transmissions (i.e., D2D transmissions) performed in the cell 21 exceeds a specified value. In Block 1202, the eNB 2 imposes, on one or more sidelink (D2D) transmitting terminals in the cell 21, a restriction regarding PSSCH resource allocation over a plurality of sidelink control periods (i.e., PSSCH periods).

Figure 13:
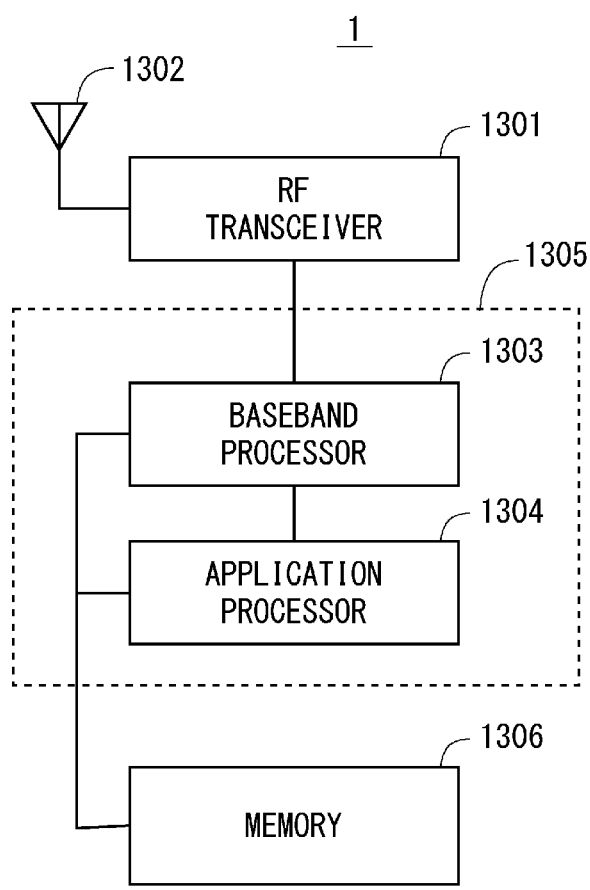
FIG. 13 is a block diagram showing a configuration example of a wireless terminal according to some embodiments.

Lastly, a configuration example of the UE 1 according to the above-described f embodiments will be described. FIG. 13 is a block diagram showing a configuration example of the UE 1. The UE 1 as the transmitting terminal and the UE 1 as the receiving terminal described above may have the configuration shown in FIG. 13. A Radio Frequency (RF) transceiver 1301 performs analog RF signal processing for communication with the eNB 2. The analog RF signal processing performed by the RF transceiver 1301 includes frequency up-conversion, frequency down-conversion, and amplification. The RF transceiver 1301 is connected to an antenna 1302 and a baseband processor 1303. Specifically, the RF transceiver 1301 receives modulated symbol data (or OFDM symbol data) from the baseband processor 1303, generates a transmission RF signal and supplies the transmission RF signal to the antenna 1302. Further, the RF transceiver 1301 generates a baseband received signal based on a received RF signal received by the antenna 1302 and supplies it to the baseband processor 1303.

The baseband processor 1303 performs digital baseband signal processing (i.e., data-plane processing) and control-plane processing for wireless communication. The digital baseband signal processing includes (a) data compression/decompression, (b) data segmentation/concatenation, (c) composition/decomposition of a transmission format (i.e., transmission frame), (d) channel encoding/decoding, (e) modulation (i.e., symbol mapping)/demodulation, and (f) OFDM symbol data (baseband OFDM signal) generation by Inverse Fast Fourier Transform (IFFT). On the other hand, the control-plane processing includes communication management of Layer 1 (e.g., transmission power control), Layer 2 (e.g., radio resource management and hybrid automatic repeat request (HARQ) processing), and Layer 3 (e.g., signaling regarding attach, mobility, and call management).

For example, in the case of LTE and LTE-Advanced, the digital baseband signal processing performed by the baseband processor 1303 may include signal processing of Packet Data Convergence Protocol (PDCP) layer, Radio Link Control (RLC) layer, MAC layer, and PHY layer. Further, the control-plane processing performed by the baseband processor 1303 may include processing of Non-Access Stratum (NAS) protocol, RRC protocol, and MAC CE.

The baseband processor 1303 may include a modem processor (e.g., Digital Signal Processor (DSP)) that performs digital baseband signal processing and a protocol stack processor (e.g., Central Processing Unit (CPU) or Micro Processing Unit (MPU)) that performs control plane processing. In this case, the protocol stack processor that performs control plane processing may be made common to an application processor 1304, which is described below.

The application processor 1304 is also referred to as a CPU, an MPU, a microprocessor or a processor core. The application processor 1304 may include a plurality of processors (a plurality of processor cores). The application processor 1304 loads a system software program (Operating System (OS)) and various application programs (e.g., voice call application, WEB browser, mailer, camera operation application, and music player application) from a memory 1306 or from another memory (not shown) and executes these programs, thereby providing various functions of the UE1.

In some implementations, as represented by a dashed line (1305) in FIG. 13, the baseband processor 1303 and the application processor 1304 may be integrated on a single chip. In other words, the baseband processor 1303 and the application processor 1304 may be implemented in a single System on Chip (SoC) device 1305. A SoC device may be referred to as a system Large Scale Integration (LSI) or a chipset.

The memory 1306 is a volatile memory, a nonvolatile memory, or a combination thereof. The memory 1306 may include a plurality of memory devices that are physically independent from each other. The volatile memory is, for example, a Static Random Access Memory (SRAM), a Dynamic RAM (DRAM), or a combination thereof. The non-volatile memory is, for example, a mask Read Only Memory (MROM), an Electrically Erasable Programmable ROM (EEPROM), a flash memory, a hard disc drive, or any combination thereof. The memory 1306 may include, for example, an external memory device that can be accessed by the baseband processor 1303, the application processor 1304, and the SoC 1305. The memory 1306 may include an internal memory device that is integrated in the baseband processor 1303, the application processor 1304, or the SoC 1305. Further, the memory 1306 may include a memory in a Universal Integrated Circuit Card (UICC).

The memory 1306 may store software module(s) (a computer program(s)) including instructions and data to perform processing by the UE 1 described in the above-described plurality of embodiments. In some implementations, the baseband processor 1303 or the application processor 1304 may be configured to load the software module(s) from the memory 1306 and execute the loaded software module(s), thereby performing the processing of the UE 1 described in the above embodiments.

Figure 14:
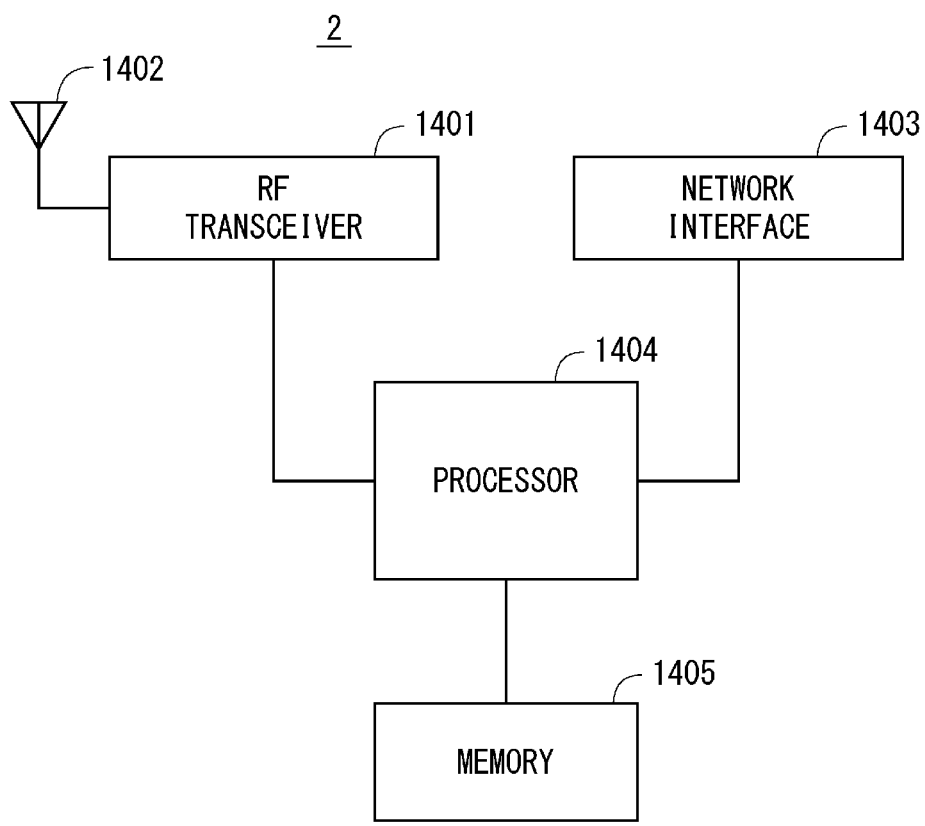
FIG. 14 is a block diagram showing a configuration example of a base station according to some embodiments.

FIG. 14 is a block diagram showing a configuration example of the base station (eNB) 2 according to the above-described embodiments. Referring to FIG. 14, the base station 2 includes an RF transceiver 1401, a network interface 1403, a processor 1404, and a memory 1405. The RF transceiver 1401 performs analog RF signal processing for communication with the wireless terminal 1. The RF transceiver 1401 may include a plurality of transceivers. The RF transceiver 1401 is connected to an antenna 1402 and a processor 1404. The RF transceiver 1401 receives modulated symbol data (or OFDM symbol data) from the processor 1404, generates a transmission RF signal and supplies the transmission RF signal to the antenna 1402. Further, the RF transceiver 1401 generates a baseband received signal based on a received RF signal received by the antenna 1402 and supplies it to the processor 1404.

The network interface 1403 is used to communicate with a network node (e.g., Mobility Management Entity (MME) and Serving Gateway (S-GW)). The network interface 1403 may include, for example, a network interface card (NIC) conforming to the IEEE 802.3 series.

The processor 1404 performs digital baseband signal processing (i.e., data-plane processing) and control-plane processing for wireless communication. For example, in the case of LTE and LTE-Advanced, the digital baseband signal processing performed by the processor 1404 may include signal processing of the PDCP layer, RLC layer, MAC layer and PHY layer. Further, the control-plane processing by the processor 1404 may include processing of S1 protocol, RRC protocol and MAC CE.

The processor 1404 may include a plurality of processors. For example, the processor 1404 may include a modem processor (e.g., DSP) that performs the digital baseband signal processing and a protocol stack processor (e.g., CPU or MPU) that performs the control-plane processing.

The memory 1405 is a combination of a volatile memory and a nonvolatile memory. The volatile memory is, for example, an SRAM, a DRAM, or a combination thereof. The nonvolatile memory is, for example, an MROM, a PROM, a flash memory, a hard disk drive, or any combination thereof. The memory 1405 may include a storage that is placed apart from the processor 1404. In this case, the processor 1404 may access the memory 1405 through the network interface 1403 or an I/O interface (not shown).

The memory 1405 may store a software module(s) (computer program(s)) including instructions and data to perform processing by the base station 2 described in the above described plurality of embodiments. In some implementations, the processor 1404 may be configured to load the software module(s) from the memory 1405 and execute the loaded software module(s), thereby performing the processing of the base station 2 described in the above described embodiments.

As described with reference to FIGS. 13 and 14, each of the processors included in the UE 1 and the eNB 2 according to the above-described embodiments executes one or more programs including a set of instructions to cause a computer to perform an algorithm described above with reference to the drawings. These programs may be stored in various types of non-transitory computer readable media and thereby supplied to computers. The non-transitory computer readable media includes various types of tangible storage media. Examples of the non-transitory computer readable media include a magnetic recording medium (such as a flexible disk, a magnetic tape, and a hard disk drive), a magneto-optic recording medium (such as a magneto-optic disk), a Compact Disc Read Only Memory (CD-ROM), CD-R, CD-R/W, and a semiconductor memory (such as a mask ROM, a Programmable ROM (PROM), an Erasable PROM (EPROM), a flash ROM, and a Random Access Memory (RAM)). These programs may be supplied to computers by using various types of transitory computer readable media. Examples of the transitory computer readable media include an electrical signal, an optical signal, and an electromagnetic wave. The transitory computer readable media can be used to supply programs to a computer through a wired communication line (e.g., electric wires and optical fibers) or a wireless communication line.

Other Embodiments

Each of the above embodiments may be used individually, or two or more of the embodiments may be appropriately combined with one another.

The above-described embodiments are not limited to LTE-Advanced and its improvements and may be applied to D2D communication in other mobile communication networks or systems.

Further, the above-described embodiments are merely examples of applications of the technical ideas obtained by the inventor. These technical ideas are not limited to the above-described embodiments and various modifications can be made thereto.

This application is based upon and claims the benefit of priority from Japanese patent application No. 2015-141124, filed on Jul. 15, 2015, the disclosure of which is incorporated herein in its entirety by reference.

REFERENCE SIGNS LIST

1 UE
2 eNB
1301 RADIO FREQUENCY (RF) TRANSCEIVER
1303 BASEBAND PROCESSOR
1304 APPLICATION PROCESSOR
1306 MEMORY
1401 RF TRANSCEIVER
1404 PROCESSOR
1405 MEMORY

The invention claimed is:

1. A transmitting terminal comprising:
at least one wireless transceiver; and
at least one processor coupled to the at least one wireless transceiver and configured to perform data transmission to another wireless terminal without going through a base station in accordance with device-to-device (D2D) control periods that occur periodically, wherein
each of the D2D control periods includes a first subframe pool consisting of a plurality of subframes usable for transmission of D2D control information and a second subframe pool consisting of a plurality of subframes usable for the data transmission in accordance with the D2D control information,
the at least one processor is configured to transmit first D2D control information in one or more subframes within the first subframe pool within a first D2D control period and perform the data transmission in accordance with the first D2D control information in one or more subframes within the second subframe pool within the first D2D control period,
the first D2D control information contains a first information element for identifying the one or more subframes within the second subframe pool within the first D2D control period, and
the first D2D control information further contains a second information element indicating whether the first D2D control information is valid in at least one D2D control period occurring after the first D2D control period,
wherein the at least one processor is further configured to impose a restriction regarding the at least one D2D control period by setting a lower limit value to a length of the at least one D2D control period under control of the base station.

2. The transmitting terminal according to claim 1, wherein the at least one processor is further configured to perform the data transmission without transmitting new D2D control information in the at least one D2D control period when the first D2D control information continues to be valid in the at least one D2D control period.

3. The transmitting terminal according to claim 1, wherein the second information element indicates a length of the at least one D2D control period.

4. The transmitting terminal according to claim 1, wherein the second information element indicates whether radio resource allocation for the data transmission based on the first D2D control information is maintained or not.

5. The transmitting terminal according to claim 1, wherein the at least one processor is further configured to transmit, in any of the at least one D2D control period, second D2D control information indicating disabling of radio resource allocation for the data transmission based on the first D2D control information.

6. The transmitting terminal according to claim 1, wherein the restriction regarding the at least one D2D control period is imposed on the transmitting terminal autonomously or under control of the base station.

7. The transmitting terminal according to claim 6, wherein the restriction includes at least one of (a) not allowing continuous enabling of the first D2D control information and (b) setting an upper limit value to a length of the at least one D2D control period.

8. The transmitting terminal according to claim 7, wherein the at least one processor is configured to, when the transmitting terminal is assumed to be located at a cell boundary between a cell of the base station and an adjacent cell, impose, on the transmitting terminal, the restriction including (a) not allowing continuous enabling of the first D2D control information or (b) setting the upper limit value to the length of the at least one D2D control period.

9. The transmitting terminal according to claim 1, wherein the at least one processor is configured to set the lower limit value under control of the base station when the number of D2D transmission performed in a cell of the base station exceeds a specified value.

10. A method in a transmitting terminal, the method comprising:
performing data transmission to a receiving terminal without going through a base station in accordance with device-to-device (D2D) control periods that occur periodically, wherein
each of the D2D control periods includes a first subframe pool consisting of a plurality of subframes usable for transmission of D2D control information and a second subframe pool consisting of a plurality of subframes usable for the data transmission in accordance with the D2D control information,
the performing the data transmission includes transmitting first D2D control information in one or more subframes within the first subframe pool within a first D2D control period and performing the data transmission in accordance with the first D2D control information in one or more subframes within the second subframe pool within the first D2D control period,
the first D2D control information contains a first information element for identifying the one or more subframes within the second subframe pool within the first D2D control period, and the first D2D control information further contains a second information element indicating whether the first D2D control information is valid in at least one D2D control period occurring after the first D2D control period,
wherein the method further comprises imposing a restriction regarding the at least one D2D control period by setting a lower limit value to a length of the at least one D2D control period under control of the base station.

11. The method according to claim 10, wherein the performing the data transmission further includes performing the data transmission without transmitting new D2D control information in the at least one D2D control period when the first D2D control information continues to be valid in the at least one D2D control period.

12. The method according to claim 10, wherein the second information element indicates a length of the at least one D2D control period.

13. The method according to claim 10, wherein the second information element indicates whether radio resource allocation for the data transmission based on the first D2D control information is maintained or not.

14. The method according to claim 10, further comprising:
transmitting, in any of the at least one D2D control period, second D2D control information indicating disabling of radio resource allocation for the data transmission based on the first D2D control information.

15. The method according to claim 10,
wherein the restriction regarding the at least one D2D control period is imposed autonomously or under control of the base station.

16. A base station comprising:
a wireless transceiver configured to communicate with a plurality of wireless terminals in a cell; and
at least one processor configured to control data transmission, the data transmission being from a first wireless terminal to a second wireless terminal without going through the base station in accordance with device-to-device (D2D) control periods that occur periodically, wherein
each of the D2D control periods includes a first subframe pool consisting of a plurality of subframes usable for transmission of D2D control information and a second subframe pool consisting of a plurality of subframes usable for the data transmission in accordance with the D2D control information, and
the at least one processor is configured to transmit, to the first wireless terminal, a D2D grant message indicating radio resource allocation for transmission of the D2D control information and the data transmission within a first D2D control period and further indicating that the radio resource allocation is valid also in at least one D2D control period occurring after the first D2D control period,
wherein the at least one processor is further configured to impose a restriction regarding the at least one D2D control period on the first wireless terminal by setting a lower limit value to a length of the at least one D2D control period.

17. The base station according to claim 16, wherein the at least one processor is configured to control the first wireless terminal to set the lower limit value when the number of D2D transmission performed in the cell exceeds a specified value.

* * * * *

UNITED STATES PATENT AND TRADEMARK OFFICE
CERTIFICATE OF CORRECTION

PATENT NO. : 10,492,098 B2  
APPLICATION NO. : 15/743156  
DATED : November 26, 2019  
INVENTOR(S) : Kazushi Muraoka and Hiroto Sugahara Page 1 of 1

It is certified that error appears in the above-identified patent and that said Letters Patent is hereby corrected as shown below:

In the Specification

Column 4, Background Art, Line 33; Delete "$(l_0^{PSCCH}, l_1^{PSCCH}, \ldots, l_{L_{PSCC}-1}^{PSCCH})$" and insert -- $(l_0^{PSCCH}, l_1^{PSCCH}, \ldots, l_{L_{PSCCH}-1}^{PSCCH})$ -- therefor Signed and Sealed this  
Twenty-fourth Day of November, 2020

Andrei Iancu  
*Director of the United States Patent and Trademark Office*